United States Patent [19]

Megyeri et al.

[11] Patent Number: 4,681,887
[45] Date of Patent: Jul. 21, 1987

[54] PHARMACEUTICAL COMPOSITIONS WITH A NEUROLEPTIC ACTION AND PROCESS FOR PREPARING SAME

[75] Inventors: Gábor Megyeri; Tibor Keve; Béla Stefkó; Erik Bogsch; János Galambos; Anna Kassainée Zieger; Ferenc Trischler; Éva Pálosi; Dóra Groó; Egon Kárpáti; Zsolt Szombathelyi; László Szporny, all of Budapest; Béla Kiss, Vecsés; István Laszlovszky; Erzsébet Lapis, both of Budapest, all of Hungary

[73] Assignee: Richter Gedeon Vegyeszeti Gyar Rt., Budapest, Hungary

[21] Appl. No.: 877,298

[22] Filed: Jun. 23, 1986

[30] Foreign Application Priority Data

Jun. 21, 1985 [HU] Hungary .............................. 2445/85

[51] Int. Cl.$^4$ ............................................ A61K 31/44
[52] U.S. Cl. ................................................... 514/284
[58] Field of Search ........................................ 514/284

[56] References Cited

PUBLICATIONS

Chem. Abst.-104-179738n (1986) referring to 1983, Acta. Pharm. Suec.
Acta. Pharm. Suec., pp. 111-119 (1983).

Primary Examiner—Stanley J. Friedman
Attorney, Agent, or Firm—Herbert Dubno; Karl F. Ross; Jonathan Myers

[57] ABSTRACT

The invention relates to pharmaceutical compositions with a neuroleptic action as well as to a process for preparing these compositions.

The active ingredients of the compositions of the invention are 2-halo-6-methyl-9-ergolene derivatives of the formula (I),

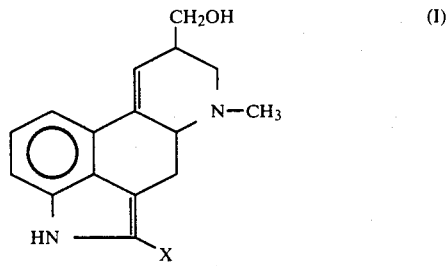

wherein
X represents a chlorine, bromine or iodine atom as well as their acid addition salts.

The compositions of the invention contain an effective dose of compound of the general formula (I) or an acid addition salt thereof.

7 Claims, No Drawings

PHARMACEUTICAL COMPOSITIONS WITH A NEUROLEPTIC ACTION AND PROCESS FOR PREPARING SAME

The invention relates to a method of treating a psychiatric disease responsive to a dopaminergic antagonist effect.

The active ingredients of the compositions of the invention are 2-halo-6-methyl-9-ergolene derivatives of the formula (I),

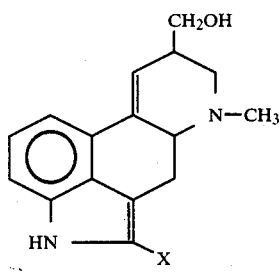

wherein X represents a chlorine, bromine or iodine atom as well as their pharmaceutically acceptable acid addition salts.

The preparation of the active ingredients of the compositions of the invention comprises
(a) halogenating lysergol (8-hydroxymethyl-6-methyl-9-ergolene) of the formula (IIa)

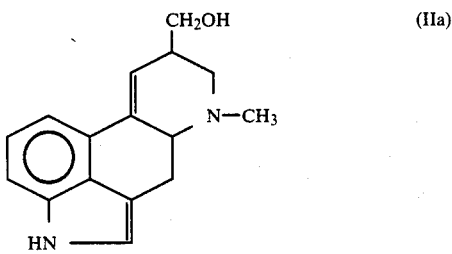

or
(b) isomerizing a 2-haloelymoclavine (2-halo-8-hydroxymethyl-6-methyl-8-ergolene) of the formula (IIb),

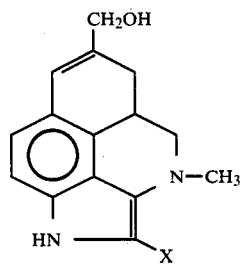

wherein X is the same as defined above, and, if desired, converting the thus-obtained 2-halo-6-methyl-9-ergolene derivative to an acid addition salt.

Of the compounds of the formula (I), 2-chlorolysergol and 2-bromolysergol have only been mentioned in one literature reference (Acta Pharm. Suec. 1983, 111-119). According to this article both compounds were found to be inactive as central dopaminergic agonists in the Ungerstedt's test.

In the course of our investigations, it has been found that the compounds of the invention possess a valuable therapeutical effect, particularly, these compounds show an antagonistic action on the D-2 receptors; thus, they exert a neuroleptic effect. Further on, these compounds are potential intermediary products for the synthesis of nicergoline (1,6-dimethyl-10-α-methoxyergolene-8β-methanol 5-bromonicotinate), a known peripheral vasodilatory drug.

The high activity of the compounds of the invention on the D-2 receptors was proved by the receptor binding test carried out by the method described below.

INVESTIGATION OF THE D-2 receptor binding

Hannover Wistar rats were decapitated and the striatum from their cortex was prepared. The striata were homogenized in a 10-fold volume of a cold buffer solution (50 mmoles of TRIS HCl, 120 mmoles of NaCl, 2 mmoles of KCl, 1 mmoles of $MgCl_2$ and 5 mmoles of $CaCl_2$, at pH 7.4) and centrifuged at 40000 g for 15 minutes. The thus-obtained sediment was suspended in the buffer in a concentration of 100 ml/g (in a protein concentration of 0.7 to 0.8 mg/ml).

For investigating the D-2 receptor binding, a membrane suspension, a buffer, a ligand (0.5 nmole of $^3H$-spiroperidol) and the compound to be tested in a defined concentration were used in a total volume of 2 ml. After an incubation at 37° C. for 15 minutes, the samples were filtered through a Whatman GF/B filter and washed 2 times with 5 ml of buffer solution each.

For the determination of the non-specific binding, 1 μmole of (+)-butaclamol was used.

A possible side-effect of the compounds, which could be expected as a consequence of their chemical structure, was investigated by the adrenergic $\alpha_1$-receptor binding assay.

INVESTIGATION OF THE $\alpha_1$-adrenergic receptor binding

Hannover Wistar rats were decapitated, their cortex were prepared and homogenized in a 20-fold volume of a buffer solution (50 mmoles of TRIS HCl, at pH 8). The membrane was centrifuged at 45000 g twice for 15 minutes and then suspended in the buffer in a concentration of 30 ml/g (in a protein concentration of 1.7 to 1.8 mg/ml).

For investigating the $\alpha_1$-receptor binding, a membrane preparation, a ligand (0.5 nmole of $^3H$-prazosine) and the compound to be tested were used in a total volume of 1 ml. After an incubation at 23° C. for 30 minutes, the samples were filtered through a Whatman GF/B filter and washed 4 times with 4 ml of buffer solution each.

For the determination of the non-specific binding, 10 μmoles of phentolamine were used.

On using both above-mentioned receptor binding methods, a scintillation solution was applied onto the filter paper in the cuvet and the isotopic radioactivity was measured on the next day.

The results of the investigations carried out by the above biochemical methods are summarized in Table 1.

TABLE 1

| | $IC_{50}$ | | $D-2/\alpha_1$ |
| --- | --- | --- | --- |
| | D-2 | $\alpha_1$ | Selectivity ratio |
| | nmole | | |
| 2-Chlorolysergol maleate | 5.3 | 45.4 | 0.12 |
| 2-Bromolysergol | 76.5 | 24.1 | 3.2 |

TABLE 1-continued

| | IC$_{50}$ | | |
|---|---|---|---|
| | D-2 | $\alpha_1$ | D-2/$\alpha_1$ |
| | nmole | | Selectivity ratio |
| maleate | | | |
| Chlorpromazine | 17.0 | 15.8 | 1.1 |

The IC$_{50}$ value means the drug concentration causing an 50% inhibition of the ligand binding.

It is obvious from the results given in the Table that the IC$_{50}$ value related to the D-2 receptors and thus, the dopaminergic activity of 2-chlorolysergol is three times as high as that of chloropromazine. Simultaneously, the side-effect on the $\alpha_1$ receptors of 2-chlorolysergol is one-third of that of chloropromazine. The substantially higher and selective D-2 receptor activity of 2-chlorolysergol as compared to that of chloropromazine is shown by the D-2/$\alpha_1$ selectivity ratio which is ten times lower.

The effect on the $\alpha_1$ receptors of 2-bromolysergol is somewhat lower than that of chloropromazine, which can also be seen from the D-2/$\alpha_1$ selectivity ratio.

The high activity on the D-2 receptors of the compounds was also supported by central nervous system studies. It was verified that the compounds possess a dopaminergic antagonist and thus, a neuroleptic action.

The neuroleptic effect of the compounds was shown by investigations on the central nervous system of Hannover Wistar rats and CFLP mice. The compounds to be tested were orally administered in a dose of 5 ml/kg of body-weight to rats or in a dose of 10 ml/kg of body-weight to mice, respectively at 60 minutes before beginning the experiment.

The compounds to be tested were suspended in TWEEN 80 and diluted to the desired concentration by adding physiological saline solution.

The results are expressed either as percentages, or ED$_{50}$ values calculated by using the probit analysis are given together with the 95% fiducial (confidential) limits (J. T. Litchfield and F. Wilcoxon: J. Pharmacol. 96, 99 (1949)).

INHIBITION OF THE CONDITIONED AVOIDANCE RESPONSE (CAR inhibition)

Male rats weighing 140 to 160 g were conditioned for 10 days in an automated six-channel shuttle box (D. Bovet et. al.: Neuropsychopharmacology, Vol. 2., p. 142 Elsevier Publishing House, Amsterdam, 1961).

Each one session consisted of 6 cycles; the time of a partial cycle was: 15 seconds for intersignal time, 15 seconds for light stimulus, 10 seconds for light stimulus and footshock (0.8 mA). The selected animals (n=6; selected on the basis of a performance higher than 80% on the 10th day) were treated with a 20 mg/kg dose of the substances before the 11th session and their performance (i.e. the mean of the number of the conditioned avoidance responses) was compared to the value obtained for each group in the previous day taken as control value. The ED$_{50}$ values are summarized in Table 2.

INVESTIGATION OF THE CATALEPTOGENIC EFFECT

The method of G. Stille and H. Launer Arzneim.-forsch. 21, 252 (1971) was used for this study.

Male rats weighing 90 to 110 g (n=5) were treated with different doses of the compounds to be tested, then the number of the animals showing catalepsy was hourly observed for 5 hours. The upper limbs of the animals were placed onto a column of 7 cm in height and the animals were considered as cataleptic when they did not correct this particular posture for 30 seconds.

INVESTIGATION OF THE AMPHETAMINE GROUP TOXICITY

The method of C. D. Proctor et al. (Arch. Int. Pharmacodyn. Ther. 163, 74 (1966)) was used for this study.

The examination was carried out on mice of both sexes weighing 22 to 27 g (n=5). At the 60th minute after administration of the substance to be tested in a dose of 30 mg/kg, d-amphetamine in a dose of 25 mg/kg was intraperitoneally given to the animals tightly closed together (25 cm$^2$/mouse) and the percentage of the perished animals was registered after 24 hours.

INHIBITION OF THE HYPERMOTILITY INDUCED BY L-DOPA (L-(3,4-dihydroxyphenyl)-$\alpha$-alanine)

The method of N. P. Plotnikoff et al. ("The Thyroid Axis, Drugs and Behavior", Raven Press, N.Y., pp. 103–113 (1974)) was used for this study.

Male mice (n=15) weighing 18 to 21 g were intraperitoneally treated with 40 mg/kg of nialamide and after 60 minutes, the substances to be tested were administered in a dose of 30 mg/kg. Thirty minutes later, 100 mg/kg of L-Dopa were intraperitoneally administered. The locomotor activity of the animals was measured by using an LKB Animex DSE motimeter in each 30th minute for 2 hours. The results are given as the percentage of the difference from the control.

INVESTIGATION OF THE APOMORPHINE HYPOTHERMIA-REVERTING EFFECT

The method of A. Barnett et al. (Arch. Int. Pharmacodyn. Ther. 198, 242 (1972)) was used for this study.

The rectal temperature of rats (n=5) was determined by using an Ellab thermometer (E3) before administering the substances to be tested in a dose of 10 mg/kg. Thereafter, 5 mg/kg of apomorphine were intraperitoneally given and the temperature of the animals was hourly registered for 3 hours. The difference of the temperature change in °C. as related to the value obtained with apomorphine are shown in Table 2.

INVESTIGATION OF THE ASPHYXIAL ANOXIA

The method of C. Caillard et al. (Life Sci. 16, 1607 (1975)) was used for this study.

Mice (n=5) of both sexes weighing 22 to 24 g were starved for 16 hours, then treated with 50 mg/kg dose of the substances to be tested. After 60 minutes, the animals were placed in tightly closed glass bottles of 100 ml volume and the survival time was registered. Those animals were considered as protected, the survival time of which was found to be longer by 30% than that of the average survival time of the control group. The ED$_{50}$ values are summarized in Table 2.

TABLE 2

| Compound administered p.o. | CAR inhibition ED$_{50}$ mg/kg | Catalepsy ED$_{50}$ mg/kg | Amphetamine group tox. ED$_{50}$ mg/kg | L-Dopa induced hypermot. inhibition % 60 min. | L-Dopa induced hypermot. inhibition % 120 min. | Apomorphine hypothermia 60 min. | Apomorphine hypothermia 120 min. | Asphyxial anoxia ED$_{50}$ mg/kg |
|---|---|---|---|---|---|---|---|---|
| 2-Chlorolysergol maleate | 3.4 | 13.6 | 28.9 | −47 | −50 | +0.9 | +1.1 | 39.8 |
| 2-Bromolysergol maleate | 2.7 | 10.8 | 10* | −60 | −65 | +1.9 | +2.4 | 35.6 |
| 2-Bromolysuride | | 3.3 | | | | | | |

*20 mg/kg p.o., 10% of mice died

It is obvious from the results summarized in Table 2 that the conditioned responses are inhibited by the 2-halogenated lysergol derivatives of the invention in a manner which is characteristic of the antipsychotic effect. The advantage of the compounds according to the invention is clear on the basis of the ED$_{50}$ values measured in this test; namely, the conditioned responses are inhibited by the compounds of the invention in doses 3 to 4 times as low as are the cataleptogenic doses. Thus, it can be expected that an extrapyramidal side-effect will only appear on administering doses which are 3 to 4 times as high as the effective antipsychotic doses. Presumably, the pharmacologic action is mediated through the dopaminergic system. This is indicated by the observation that the L-dopa-induced locomotor hyperactivity is inhibited and the apomorphine-induced hypothermia is reverted by the substances tested.

In conclusion, the strong dopaminergic activity of 2-halolysergol derivatives is well supported by the above biochemical and pharmacological results. This dopaminergic effect is antagonistic in character, though an agonistic action could be expected on the basis of the chemical structure.

The invention is described in detail hereinafter.

According to the process (a) of the invention, lysergol as starting substance is halogenated to give the corresponding 2-haloderivative, i.e. a 2-halo-lysergol. For preparing the compounds of the formula (I) containing a chlorine atom as X the chlorination is carried out in such a way that lysergol dissolved in dimethylsulphoxide is saturated with dry gaseous hydrogen chloride and the mixture is allowed to stand at room temperature for some hours. Thus, the starting substances are converted to the appropriate 2-chloro derivatives. Then, the reaction mixture is poured into ice-water, alkalinized by adding aqueous ammonia and the precipitate is filtered off. The chlorination may also be achieved by dissolving the starting lysergol in anhydrous tetrahydrofuran and adding a molar equivalent of tert.-butyl hypochlorite while stirring. Then, the mixture is let to stand at room temperature for about 20 minutes, evaporated under reduced pressure and purified by column chromatography.

For the preparation of the compounds of the formula (I) containing a bromine atom as X, the bromination is preferably carried out by using N-bromosuccinimide. This reaction is carried out in an ether-type solvent such as dioxane at a temperature between 20° C. and 60° C. by dissolving the starting lysergol in hot dioxane and adding dropwise a solution containing N-bromosuccinimide in dioxane under stirring. This reaction proceeds at 60° C. within about 30 minutes. Thereafter, the mixture is alkalinized and evaporated under reduced pressure and the 2-bromo derivatives are isolated by column chromatography.

For preparing the compounds of the formula (I) containing an iodine atom as X, the iodination is preferably achieved by using N-iodosuccinimide. This reaction is carried out in an aprotic solvent, preferably in a similar manner as described for the bromination.

According to the process (b) of the invention, the starting 2-haloelymoclavine derivative is isomerized to give the desired 2-halo-6-methyl-9-ergolene derivative of the general formula (I). To this isomerization an activated aluminium oxide catalyst is preferably used the water content of which is adjusted to the desired 0.01 to 3% after the determination of its activity, either by adding a calculated amount of water or by removing the excess water by azeotropic distillation or drying.

The starting compound and the catalyst are suspended in an aromatic hydrocarbon such as benzene or toluene, preferably in toluene and boiled for 15 minutes for completion of the isomerization. The product is separated from the catalyst by dissolving an aliphatic alcohol, preferably methanol, and the solution is evaporated under reduced pressure to obtain the desired 2-halo-6-methyl-9-ergolene derivative.

If desired, the compounds of the formula (I) prepared by using the process (a) or (b) of the invention are purified by recrystallization or, if desired, converted to acid addition salts by using an appropriate acid.

The recrystallization may be performed from an aliphatic alcohol, preferably ethanol, or from a mixture of an aliphatic alcohol with a chlorinated hydrocarbon, e.g. from a 1:2 mixture of chloroform with ethanol.

The salt formation can be performed in an organic solvent or in water or in a mixture of these solvents, e.g. in an aliphatic alcohol, ether, acetone, ethyl acetate, acetonitrile, preferably water in such a manner that a 2-halo-6-methyl-9-ergolene base of the formula (I) is dissolved at 80° to 90° C. in a solution containing the appropriate acid in a concentration of 3 to 5% in one of the above solvents, then the mixture is cooled to room temperature. The precipitated acid addition salts are separated by filtration. Mono- or polyvalent organic or inorganic acids such as phosphoric, acetic, methanesulphonic, camphorsulphonic, sulphuric, perchloric, maleic and tartaric acid, preferably phosphoric acid, may be used for the salt formation.

The active ingredients of the formula (I) can be converted into pharmaceutical compositions by mixing them with the usual non-toxic, inert, solid or liquid carriers and/or auxiliary agents which are commonly used in compositions for enteral or parenteral administration. As carriers e.g. water, gelatine, lactose, starch, pectin, magnesium stearate, stearic acid and vegetable oils such as peanut oil or olive oil, or the like can be employed. The active ingredient can be formulated to the usual pharmaceutical compositions, particularly to solid forms such as tablets; dragées; capsules, e.g. gelatine capsules; pills; suppositories; or the like. The amount of the solid materials can vary between wide limits, preferably they are used in an amount between about 25 mg and 1 g. The compositions may optionally contain commonly used pharmaceutical additives, e.g. preserving agents, stabilizers, wetting agents, emulsifying agents, or the like. The compositions can be prepared by using methods commonly employed in the pharmaceutical industry.

Tablets can be prepared e.g. by wet granulation and subsequent compression. The active ingredients, carriers and optionally a part of the disintegrating additives mixed together are granulated together with an aqueous, ethanolic or aqueous-ethanolic solution of the binding agent in an appropriate equipment, then the granulate is dried. Thereafter, the other disintegrating, sliding and anti-adhesive additives are mixed into the dried granulate, then the mixture is transformed to tablets by compression. In order to promote the administration, the tablets may be provided with a division mark. Alternatively, the tablets may directly be produced from the mixture of the active ingredient and the suitable additives by compression. Optionally, the tablets can be transformed to dragées by using coating, aromatizing and coloring agents such as sugar, cellulose derivatives (e.g. methyl- or ethylcellulose, carboxymethylcellulose sodium or the like), polyvinylpyrrolidone, calcium phosphate, calcium carbonate, food dyes, food dye lacquers, aromatizing agents, iron oxide pigments, or the like. For the preparation of capsules, a mixture containing the active ingredient together with the auxiliary materials is filled into the capsule.

For the purpose of the rectal administration, the composition is formulated into suppositories. In addition to the active ingredient, the suppository contains a carrier mass, the so-called suppository adeps. Fats of plant origin, e.g. hardened vegetable oils such as triglycerides of $C_{12-18}$ fatty acids, preferably carriers of the trade name Witepsol ® may be used. The active ingredient is homogeneously distributed in the molten carrier mass, then the suppositories are prepared by a moulding process.

For the parenteral route of application, the composition is formulated in injectable solutions. For preparing these solutions, the active ingredients are dissolved in distilled water and/or various organic solvents such as glycol ethers or alcohols, optionally in the presence of solubilizing agents such as polyoxyethylene sorbitan monolaurate, -monooleate or -monostearate (Tween 20, Tween 60, Tween 80). In addition, the injectable solutions may contain various auxiliary materials such as: preserving agents, e.g. benzyl alcohol, methyl 4-hydroxybenzoate or propyl 4-hydroxybenzoate, benzalkonium chloride or phenylmercuryborate or the like; antioxidants, e.g. ascorbic acid, tocopherol or sodium pyrosulphate; and optionally, for binding metal traces, a complex forming agent such as ethylenediamine tetraacetate; further on, pH-adjusting and buffer substances; as well as optionally a local anaesthetic drug, e.g. lidocaine. Before filling into the ampouls, the injectable solution containing the pharmaceutical composition of the invention is filtered and sterilized after the filling.

The pharmaceutical compositions are suitably shaped in such a manner that one dosage unit or a very low number of the dosage units (tablet, dragée, bag, capsule, suppository, drop or teaspoon) contains a single dose.

Of course, the dosage unit may contain a low manifold of the single dose. For this purpose, the tablets may be provided e.g. with a division mark promoting the easy breaking of the tablets.

On using the pharmaceutical composition, the patient is treated with an amount containing the active ingredient in a dose needed to ensure the desired effect. This dose depends upon the severity of the disease, on the body-weight and the sensitivity against the active ingredient of the patient as well as on the route of the administration and the number of the daily treatments. The dose to be used in a given occasion can easily be defined by the physician with the knowledge of the patient.

The pharmaceutical compositions according to the invention contain the active ingredient of the invention in an effective single dose of 0.005 to 5 mg/kg of body-weight. However, the quantity of the active ingredient may, of course, be more or less than the above-defined limits.

The invention also relates to a method for treating psychiatric diseases. This process comprises the use of a therapeutically effective amount of a pharmaceutical composition of the invention.

The invention is illustrated in detail by the aid of the following non-limiting Examples.

The pharmaceutical compositions with the following ingredients may e.g. be prepared by using the novel compounds of the invention.

EXAMPLE 1

Preparation of tablets 10 g of the active ingredient, 120 g of lactose, 50 g of potato starch, 4 g of polyvinyl pyrrolidone, 6 g of talc, 1 g of magnesium stearate, 1 g of colloidal silicon dioxide (Aerosil) and 6 g of ultra-amylopectin are mixed together and after wet granulation, tablets weighing 200 mg and containing 10 mg of the active ingredient each are prepared by compression.

In this case, the active ingredient is 2-chlorolysergol maleate.

EXAMPLE 2

Preparation of dragées

The tablets prepared as described above are covered in a manner known per se with a coating consisting of sugar and talc. The dragées are polished by using a mixture of bee wax and carnauba wax.

Each dragée weighes 250 mg.

EXAMPLE 3

Preparation of an injectable solution

| Ingredient | g |
| --- | --- |
| 2-Chlorolysergol maleate | 0.5 |
| Propyl 4-hydroxybenzoate | 0.02 |
| Acetic acid (98%) | 0.025 |
| Sodium acetate trihydrate | 0.06 |
| Methyl 4-hydroxybenzoate | 0.13 |
| Ethanol (96%) | 5 |
| Mannitol | 10 |
| Distilled water for injection purpose up to | 100 ml |

Mannitol and sodium acetate are dissolved in an aliquot quantity of freshly boiled, nitrogen-saturated, distilled water of injectable quality (for injection purpose) and the above-defined amount of acetic acid is added. 2-Chlorolysergol maleate, propyl 4-hydroxybenzoate and methyl 4-hydroxybenzoate are dissolved in 96% ethanol and the thus-obtained solution is mixed with the solution prepared as described above. The solution is filled up to the final volume by adding distilled water of injectable quality (for injection purpose), the solution is homogenized, subjected to sterile filtration and filled to glass bottles previously sterilized in an inert gas. The concentration of the active ingredient is 5 mg/ml.

We claim:

1. A method of treating a psychiatric disease responsive to a dopaminergic antagonistic effect in a mammalian subject needing said treatment which comprises the step of administering to said mammalian subject a therapeutically effective amount of a compound of the Formula (I)

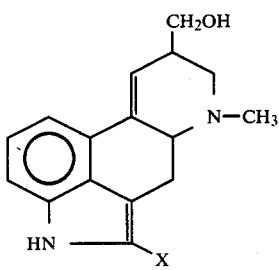

wherein X is chloro, bromo, or iodo; or a pharmaceutically acceptable acid addition salt thereof.

2. The method of treating the pyschiatric disease defined in claim 1 wherein the pharmaceutically acceptable acid addition salt of the compound of the Formula (I) is 2-chlorolysergol maleate.

3. The method of treating the psychiatric disease defined in claim 1 wherein the pharmaceutically acceptable acid addition salt of the compound of the Formula (I) is 2-bromolysergol maleate.

4. The method of treating the psychiatric disease defined in claim 1 wherein the compound of pharmaceutically acceptable acid addition salt of the Formula (I) is orally administered.

5. The method of treating the psychiatric disease defined in claim 1 wherein the compound or pharmaceutically acceptable acid addition salt of the Formula (I) is rectally administered.

6. The method of treating the psychiatric disease defined in claim 1 wherein the compound or pharmaceutically acceptable acid addition salt of the Formula (I) is parenterally administered.

7. The method of treating the psychiatric disease defined in claim 1 wherein the compound or pharmaceutically acceptable acid addition salt of the Formula (I) is administered in a dose of 0.005 to 5 mg/kg of body weight.

* * * * *